United States Patent [19]

Gupta et al.

[11] Patent Number: 4,957,866
[45] Date of Patent: Sep. 18, 1990

[54] METHOD FOR REPRODUCING CONIFEROUS PLANTS BY SOMATIC EMBRYOGENESIS

[75] Inventors: Pramod K. Gupta, Federal Way; Gerald S. Pullman, Renton, both of Wash.

[73] Assignee: Weyerhaeuser Company, Tacoma, Wash.

[21] Appl. No.: 321,035

[22] Filed: Mar. 9, 1989

[51] Int. Cl.$^5$ .......................... A01H 4/00; A01H 7/00
[52] U.S. Cl. ............................ 435/240.4; 435/240.45; 435/240.48; 435/240.54; 47/58
[58] Field of Search ........... 435/240.4, 240.45, 240.48, 435/240.54; 47/58

[56] References Cited

U.S. PATENT DOCUMENTS 4,217,730  8/1980  Gupta et al. ............................. 47/58

OTHER PUBLICATIONS

Schuller et al. (1989), *Plant Cell, Tissue & Orgon Culture*, vol. 17, pp. 53–58.
Becwar et al. (1988), in Somatic Cell Genetics of Woody Plants, Editor M. R. Ahuja, Kluwer Acadenic Press. pp. 1–18.
Lelu (1988), Annales de Researches Silvicoles, AFOCEL, Paris, pp. 35–47.
Lelu et al. (1987), C.R. Acad. Sci., Paris, 305, Series 3, pp. 105–109.
Krogstrup (1986), *Canadian Journal of Forestry Research*, vol. 16, pp. 664–668.
Finer et al. (1989), *Plant Cell Reports*, vol. 8: pp. 203–206.
Verttagen et al. (1989), *Plant Cell, Tissue and Organ Culture*, vol. 16, pp. 103–111.
Gupta et al. (1987), *Bio/Technology*, vol. 5, pp. 710–712.
Boiko (1977), *Fizidogiyai Biokhimiya Kul'turnykh Rustenii*, 9(6), 637–641.
Kisha (1987), *Plant Science*, 48(3): 189–194.
Van Arnold (1987), *J. Plant Physiology*, vol. 128(3) pp. 233–244.
Abstracts, 4th International Conifer Tissue Culture Work Group, Aug. 8–12, 1988.
*Plant Cell Reports*, 7:445–448, Bourkgard, F. & J. M. Favre, 1988.
*Plant Science*, 52:229–235, Durzan, D. J. & P. K. Gupta, 1987.
*Plant Cell Reports*, 4:177–179, Gupta, Pramod K. & Don J. Durzan, 1985.

(List continue on next page.)

Primary Examiner—Charles F. Warren
Assistant Examiner—Gary Benzion

[57] ABSTRACT

The present invention is a method for reproducing coniferous trees by somatic embryogenesis using plant tissue culture techniques. The method comprises a multistage culturing process. A suitable explant, typically the fertilized embryo excised from a mature or immature seed, is first cultured on a medium that induces multiple early stage proembryos. Preferably the proembryos from the indication stage are further multiplied in a second culture having reduced growth hormones. The early stage proembryos are then placed in or on a late stage proembryo development culture having a significantly higher osmotic potential than the previous stage or stages. This increased osmotic potential medium is a critical key to the development of very robust late stage proembryos having at least about 100 cells and multiple suspensor cells. Culturing from this point coninues in an embryo development medium very low in or lacking growth hormones but containing abscisic acid. After a period of several weeks cotyledonary embryos will have formed. These have a well defined bipolar structure with cotyledonary primordia at one end and a latent radicle at the other. Culturing to this point is carried out in darkness or greatly subdued light. The cotyledonary embryos are then transferred to a growth medium with a light/dark photoperiod for development of plantlets. The plantlets may then be transplanted to soil for further growth. The method has been successful with a broad range of species and with numerous genotypes that could not previously be propagated by embryogenesis.

24 Claims, 1 Drawing Sheet

OTHER PUBLICATIONS

*Bio/Technology,* 4:643–645, Gupta, Pramod K. & Don J. Durzan, 1986.
*Bio/Technology,* 5:145–151, Gupta, Pramod K. & Don J. Durzan, 1986.
*Journal of Plant Physiology,* 121:149–158, Hakman, Inger & Sara Von Arnold, 1985.
*Plant Science,* 38:53–59, Hakman, Inger, Larry C. Fowke, Sara von Arnold and Tage Eriksson, 1985.
*Physiologia Plantarum,* 15:473–492, Murashige, T. and F., Skoog, 1962.
*Canadian Journal of Forest Research,* 15:1088–1091, Nagmani, R. and J. M. Bonga, 1985.
"Embryo" in Embroyology of Gymnosperms, Chapter 11, Berbruder Borntrager, Berlin, Singth, Hardev, 1978.
*Plant Physiology,* 82:942–945, Teasdale, Robert D., Pamela A. Dawson, Harold W. Woolhouse, 1986.

METHOD FOR REPRODUCING CONIFEROUS PLANTS BY SOMATIC EMBRYOGENESIS

BACKGROUND OF THE INVENTION

The present invention is a method for reproducing coniferous plants by somatic embryogenesis using the techniques of plant tissue culture. It is especially suited for producing large clones of superior trees useful for reforestation.

Loblolly pine (*Pinus taeda*), its closely related southern pines, and Douglas-fir (*Pseudotsuga menziesii*) are probably the most important commercial species of temperate North American timber trees. Since the early 1940s, when serious private reforestation efforts began, literally billions of one and two year old nursery-grown trees have been planted on cut-over or burned forest lands. For many years these seedling trees were grown using naturally produced seed from cones collected as a part time effort of individuals seeking to supplement their incomes. As early as 1957 forest geneticists began to plant seed orchards using either seed or grafted scions obtained from superior trees. These trees were selected for such inheritable characteristics as rapid growth, straightness of bole, wood density, etc. Now in both the southern pine and Douglas-fir regions the bulk of the seed is produced from selected trees grown in seed orchards, some of them now second generation orchards.

Despite the fact that the orchards were stock with superior trees, pollination often cannot be carefully controlled and frequently the seed trees are fertilized by wild pollen of unknown characteristics. For this reason, the characteristics of the progeny produced by sexual reproduction have not been as predictable as hoped and genetic gain could not be attained as rapidly as desired.

Beginning about 1960, techniques were developed for reproducing some species of plants by tissue culture. These were predominantely angiosperms and usually ornamental house plants. The method employed use of a suitable explant or donor tissue from a desirable plant. This was placed on a series of culture media in which nutrients and growth hormones were carefully controlled from step to step. The usual progression was growth from the explant to a callus. The callus was placed on a budding medium where adventitious buds formed. These, in turn, were separated, elongated, and rooted to ultimately form plantlets. A plantlet has the nature of a seedling but is genetically identical to the explant donor plant.

Gymnosperms in general, and most forest tree species in particular, proved to be much more difficult to reproduce by tissue culture. It was not until about 1975 that Douglas-fir was successfully reproduced by organogenesis. Loblolly pine was successfully reproduced about two years later.

Culture by organogenesis is tedious and expensive due to the large amount of delicate manual handling necessary. It was soon recognized that embryogenesis was potentially a much more desirable method from the standpoints of quantity of plantlets produced, cost, and potential genetic gain. Work on embryogenesis of forest species began in the late 1970s. U.S. Pat. No. 4,217,730 to El-Nil describes one early process for embryogenesis of Douglas-fir. This approach was later set aside because advanced stage embryos and plantlets could not be readily obtained. However, other workers entered the field in increasing numbers and progress has been rapid even if it has not until the present time reached the commercial stage. A brief review of some of the most important work will follow. This is intended to be representative and is not fully inclusive of all the work in the field. For the convenience of the reader, citations in the text are given in abbreviated form. Reference should be made to the bibliography at the end of the specification for full details of the literature cited.

The natural embryogeny of gymnosperms is described in great detail by Singh (1978). Conifer-type embryogeny is one of four types noted for gymnosperms. This includes virtually all of the important forest species except Sequoia.

Bourgkard and Favre (1988) describe what is the apparently successful production of plantlets by somatic embryogenesis of *Sequoia sempervirens*. As a historic note, this was one of the first forest tree species successfully reproduced by organogenesis.

Hakman and her coworkers have concentrated on Norway spruce (*Picea abies*), apparently with some success. In a paper by Hakman, Fowke, von Arnold, and Eriksson (1985) the authors describe the production of "embryos" but not plantlets. Hakman and von Arnold (1985) do suggest that they have successfully obtained plantlets. This latter paper is interesting for its comments on the variability within the species and the poor success with many of the seed sources used for explants. The authors suggest that this variability may be due to the physiological condition of the source material. However, other workers have noted great differences in behavior between recognized genotypes of the species.

Nagmani and Bonga (1985) describe embryogenesis from megagametophytes of *Larix decidua* by tissue culture. Some of the resulting embryos were stated to have further advanced to become plantlets of unknown ploidy established in soil.

Successful production of small quantities of plantlets has now been reported for loblolly pine. Teasdale, Dawson, and Woolhouse (1986) showed the criticality of proper mineral nutrients for cell suspension cultures of loblolly pine. The article by Becwar, Wann, and Nagmani (1988) is enlighting for the differences shown in performance between different families (or genotypes). Three families out of the ten tried accounted for most of their success. Even so, they appeared unable to grow cotyledonary embryos. A companion paper by Nagmani and Becwar (1988) showed development of *Pinus taeda* to the precotyledonary stage. In an earlier paper, Gupta and Durzan (1987) described their success in taking loblolly pine to the plantlet stage by embryogenesis. However, only one genotype was successfully taken to the plantlet stage and only one plantlet was produced. The authors note the need for "improved conversion rates" as well as other information before the process can be considered commercially practical.

Sugar pine (*Pinus lambertiana*) has also been cultured to the plantlet stage as reported by Gupta and Durzan (1986). The authors note a very low 1-2% conversion of embryos into plantlets.

The above researchers have also had success in producing Douglas-fir plantlets (Durzan and Gupta 1987). Again, the success ratio appears to be very low and with only a single genotype.

While the potential for achieving genetic gain using somatic embryogenesis is recognized as being very great, the problems to date have been so overwhelming that no commercial application has seemed close at hand for forest species. In fact, oil palm is the only tree reproduced by embryogenesis to have reached the stage of small plantation plantings. Until the present invention, possible commercial production of timber species by embryogenesis has remained no more than a fond hope in the minds of the people working in the field.

SUMMARY OF THE INVENTION

The present invention is a method of reproducing selected plants by somatic embryogenesis using tissue culture techniques. The method is particularly suitable for reproducing woody gymnosperms of the order Coniferales. It is especially well suited for generating large clones of superior forest trees for reforestation, including, species within the families Pinaceae, Cupressaceae, and Taxodiaceae. Most or all species within the genera Pinus, Picea, Tsuga, Pseudotsuga, Thuja, Juniperis, Larix, and Sequoia are believed to be well suited for multiplication by the present method.

A number of terms are known to have differing meanings when used in the literature. The following definitions are believed to be the ones most generally used in the field of botany and are consistent with the usage of the terms in the present specification.

"Auxins" are plant hormones that promote cell division and growth.

"Cytokinins" are plant hormones that affect the organization of dividing cells.

"Callus" is generally considered to be a growth of unorganized and either unconnected or loosely connected plant cells generally produced from culturing an explant.

"Embryogenic callus" is a callus-like mass that contains early stage proembryos attached to suspensors.

A "proembryo" is a cell or group of cells having the potential to become a plant but lacking defined meristematic organ primordia.

An "early stage proembryo" is a mass generally of 1–10 cells with dense cytoplasm and large nuclei that have the potential of forming a plant. The early stage proembryo is normally found as a head associated at the end of a long thin-walled suspensor cell.

A "late stage proembryo" is a proembryo with a smooth embryonal head of at least about 100 cells associated with multiple suspensor cells. The late stage proembryo is a very robust advanced proembryo.

A "cotyledonary embryo", sometimes simply referred to as an "embryo", has a well defined elongated bipolar structure with latent meristem with cotyledonary primordia at one end and a potential radicle at the opposite end. The cotyledonary structure frequently appears as a small "crown" at one end of the embryo.

An "explant" is a piece of tissue taken from a donor plant for culturing.

A "meristem" or "meristematic center" is a group of tissue forming cells capable of further development into plant organs; e.g., shoots and roots.

An "osmoticant" is a chemical material used for controlling the osmotic potential of a solution. In the present context the solution would be a culture medium.

A "plantlet" is a plant asexually reproduced by tissue culture.

"Somatic embryogenesis" is the process using tissue culture techniques for generating multiple embryos from an explant. The embryos from a given tissue source and presumed to be genetically.

The present method comprises a multistage culturing process. A suitable explant is first placed on an induction culture medium. This usually will contain relatively high quantities of growth hormones including at least one auxin and frequently one or more cytokinins. However, growth hormones at this initial stage are not always necessary or desirable for induction of early stage proembryos. A number of sources of explants may ultimately prove to be satisfactory for culturing. These include, but are not limited to, tissue from cotyledons, hypocotyls, epicotyls, buds, meristematic centers for buds or roots, and seed embryos. Seed embryos are presently preferred. In particular, for species which in the past have proved to be very difficult or impossible to propagate by somatic embryogenesis, the embryos from immature seeds are highly preferred at the present time.

The first stage or induction medium will normally be one of those well known from past work which contain a balanced concentration of inorganic salts and organic nutrient materials, with plant growth hormones included as noted above. Auxins are normally present in concentrations in the neighborhood of about 250 $\mu$M/L, more typically not exceeding about 50 $\mu$M/L. Cytokinins, if present, are usually in the neighborhood of 40–50 $\mu$M/L. The hormones may include at least one auxin and one cytokinin in a combined concentration not exceeding about 250 $\mu$M, more typically not exceeding about 100 $\mu$M. The particular auxins and cytokinins used and their exact concentrations, or whether they are used at all, will depende somewhat on the species being cultured and even on the particular genotype within that species. This is something that cannot be readily predicted but can easily be determined experimentally. Culturing during this stage is normally carried out in the dark or under very low light conditions until an embryogenic mass forms. This embryogenic mass has been described by various other names by researchers who have reported it in the past; e.g., embryogenic callus (Hakman and von Arnold 1985) or embryonal-suspensor mass (Durzan and Gupta 1987). It has the appearance of a whitish translucent mucilagenous mass containing early stage proembryos which are readily apparent by low power light microscopy.

Early stage proembryos from the first culture may be directly transferred to a late proembryo development culture medium having significantly reduced plant growth hormones and a higher concentration of osmoticants. However, they are preferably first subcultured in a maintenance medium of similar osmotic potential to the induction medium for multiplication. This multiplication medium will also typically have the concentration of plant hormones significantly reduced below that of the induction medium. By "significantly reduced"0 is meant lowered by a factor which may typically be one whole order of magnitude.

The composition and use of the late proembryo development culture medium is critical to the success of the present process. It differs from the induction medium by having the reduced level of plant growth hormones present in the maintenance and multiplication medium. However, it differs from either of these earlier media by having the concentration of osmoticants significantly raised above that of the induction or multplication media. Osmoticant concentration must be sufficient to raise the osmotic potential into the range of 200–400 mM/kg. This is compared with a preferred osmotic potential in the induction and maintenance media of less than about 200 mM/kg, preferably less than about 175 mM/kg and most preferably less than about 160 mM/kg.

Incubation is carried out in the dark or in greatly reduced light until robust late stage proembyros have formed. These may then be transferred to an embryo development medium which preferably lacks growth hormones entirely and has the level of osmoticants reduced back to that of the induction medium. A low concentration of abscisic acid is a necessary new component in this medium. After an appropriate length of time, again under dark or greatly reduced light photoconditions, cotyledonary embryos will form. These may be transferred to a final medium for germination. The germination medium has no hormones, a greatly lowered organic nitrogen content, and a further reduced level of osmoticants. After a sufficient time under a 16 hour light and 8 hour dark photoperiod the cotyledonary embryos will have developed into plantlets. These have a well developed radicle and cotyledonary structure and are ready for planting in soil.

It is an object of the present invention to produce coniferous plantlets by somatic embryogenesis.

It is another object to produce a large clone of a genetically selected forest species for reforestation using the methods of somatic embryogensis and plant tissue culture.

It is a further object to provide a method of somatic embryogenesis that will dependably and consistently provide coniferous plantlets in large quantities.

It is yet another object to provide a method of somatic embryogensis that can dependably and consistently reproduce large clones of selected individuals of forest species that heretofore have not been successfully reproduced by this method.

It is still a further object to provide a method whereby superior genotypes of coniferous trees can be multiplied by tissue culture in the large quantities needed for reforestation.

These and many other objects will become readily apparent to those skilled in the art by reading the following detailed description, taken in conjunction with the drawings.

BRIEF DESCRIPTION OF THE DRAWINGS

The figures show various stages of plant embryogenesis in which.

DETAILED DESCRIPTION OF THE PREFERRED EMBODIMENTS

Figure 1:
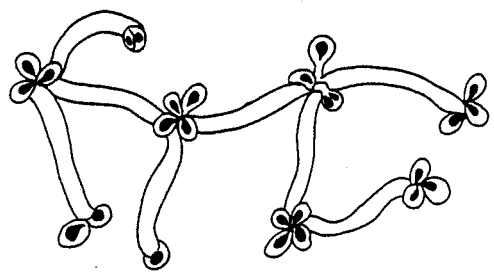
FIG. 1 shows early stage proembryos.

The process of the present invention is not limited to any single culture medium or to the use of specific growth hormones. Any of a number of well known media, such as that of Murashige and Skoog (1962), may be used. However, the present inventors have found the basal medium described in Table 1 to give excellent results, particularly when used for culturing loblolly pine (*Pinus taeda*). The basal medium is modified for each of the various culturing stages as shown in Table 2.

TABLE 1

| Basal Medium (Modified ¼ P6 Basal Salts*) | |
|---|---|
| Constitient | Concentration, mg/L |
| $NH_4NO_3$ | 603.8 |
| $KNO_3$ | 909.9 |
| $KH_2PO_4$ | 136.1 |
| $Ca(NO_3)_2 \cdot 4H_2O$ | 236.2 |
| $MgSO_4 \cdot 7H_2O$ | 246.5 |
| $Mg(NO_3)_2 \cdot 6H_2O$ | 256.5 |
| $MgCl_2 \cdot 6H_2O$ | 101.7 |
| KI | 4.15 |
| $H_3BO_3$ | 15.5 |
| $MnSO_4 \cdot H_2O$ | 10.5 |
| $ZnSO_4 \cdot 7H_2O$ | 14.4 |
| $NaMoO_4 \cdot 2H_2O$ | 0.125 |
| $CuSO_4 \cdot 5H_2O$ | 0.125 |
| $CoCl_2 \cdot 6H_2O$ | 0.125 |
| $FeSO_4 \cdot 7H_2O$ | 6.95 |
| $Na_2EDTA$ | 9.33 |
| Sucrose | 30,000. |
| myo-Inositol | 1,000. |
| Casein hydrolysate | 500.0 |
| Glutamine | 450.0 |
| Thiamine.HCl | 1.00 |
| Pyridoxine.HCl | 0.50 |
| Nicotinic acid | 0.50 |
| Glycine | 2.00 |
| Difco agar | 6,000. |
| pH adjusted to 5.7 | |

*According to Teasdale, Dawson, and Woolhouse (1986)

TABLE 2

| Composition of Media for Different Stage Treatments |
|---|
| $BM_1$ Induction Medium |
|     BM + 2,4-D (50 μM) + KIN (20 μM) + BAP (20 μM) |
| $BM_2$ Maintenance and Multiplication Medium |
|     BM + 2,4-D (5 μM) + KIN (2 μM) + BAP (2 μM) |
| $BM_3$ Late Proembryo Development Medium |
|     $BM_2$ + 9000 mg/L myo-inositol |
| $BM_4$ Embryo Development Medium |
|     BM + 4.0 to 8.0 mg/L abscisic acid |
| $BM_5$ Germination Medium |
|     BM modified by reducing sucrose to 20,000 mg/L, myo-inositol to 100.0 mg/L, glutamine to 200.0 mg/L, and casein hydrolysate to 0.0 mg/L |

A number of abbreviations are used in the following text. These are in common use in the field of tissue culture.
BAP—$N^6$-benzylaminopurine (or $N^6$-benzyladenine), a cytokinin
KIN—kinetin (6-furfurylaminopurine), also a cytokinin
2,4-D—2,4-dichlorophenoxyacetic acid, an auxin.

It will be understood by those skilled in the art that other plant growth hormones can be substituted for those just noted. As examples, IAA (indole-3-acetic acid), IBA (indole-3-butyric acid), and NAA (naphthalene-2-acetic acid) are effective auxins and 2-IP ($N^6$-isopentenylaminopurine) is frequently used as a cytokinin.

A critical key to the present invention is the careful control of the osmotic potential of each of the media used in the various culturing stages. A large group of chemical materials are suitable as osmoticants. In general these are highly water soluble polyhydroxylated molecules that include either simple or complex sugars, hexitols, and cyclitols. The cyclitols are normally six carbon ring compounds that are hexahydroxylated. The most readily available cyclitol is myo-inositol but any of the other eight stereoisomeric forms, such as scyllo-inositol are believed to be quite suitable. Among the sugars, sucrose and glucose are known to be very effective but many others should prove to be equally useful.

Sorbitol (D-glucitol), D-mannitol, and galactitol (dulcitol) are straight chain sugar alcohols suitable as osmoticants. Other materials suitable as osmoticants may include glycol ethers such as poly(ethylene glycol) and poly(propylene glycol).

EXAMPLE 1

The following schedule of treatments has been very successfully used for the growth of plantlets by somatic embryogenesis of loblolly pine (*Pinus taeda*). Explants were immature embryos dissected from seeds 4 to 5 weeks after fertilization. Seeds were obtained from cones supplied by a Weyerhaeuser Company seed orchard located at Washington, N.C. The cones were stored at 4° C. until used. Immediately before removal of the immature embryos the seeds were sterilized using a modified method of Gupta and Durzan (1985). Briefly, this involves an initial washing and detergent treatment followed by a first sterilization in 30% $H_2O_2$ and a second in diluted 10% v/v household bleach. The additional $HgCl_2$ treatment used by Gupta and Durzan was not found to be necessary to ensure sterility. The explants were thoroughly washed with sterile distilled water after each treatment.

Stage I—Induction

Sterile dissected embryos were placed on a solid $BM_1$ culture medium and held in an environment at 22°–25° C. with a 24 hour dark photoperiod for a time of 3–5 weeks. The length of time depended on the particular genotype being cultured. At the end of this time a white mucilagenous mass had formed in association with the original explants. This appears to be identical with that described by Gupta and Durzan (1987). Microscopic examination revealed numerous early stage proembryos associated with the mass. These are generally characterized as having a long thin-walled suspensor associated with a small head generally having less than 10 individual cells, each with dense cytoplasm and large nuclei. Early proembyros are illustrated in FIG. 1.

Osmolality of the induction medium may in some instances be as high as 200 mM/kg. Normally it will be below 175 mM/kg and, more typically, about 160 mM/kg or even lower. The osmolality of the medium described above was 158 mM/kg.

Stage II—Maintenance and Multiplication

Early stage proembryos removed from the masses generated in the induction stage were placed on a $BM_2$ medium. This differs from the induction medium in that the growth hormones (both auxins and cytokinins) were reduced fy a full order of magnitude. The temperature and photoperiod were again 22°–25° C. with 24 hours in the dark. Osmolality of this medium will typically be similar to identical to that of the induction medium. In the present example it was identical. Proembryos developed in this stage were similar in appearance to those from Stage 1 and were subcultured every 12–15 days on $BM_2$ medium.

Stage III—Later Stage Proembryo Development

Figure 2:
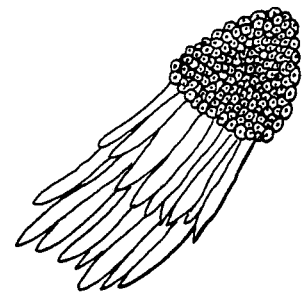
FIG. 2 shows late stage proembryos.

Early stage proembryos from either Stage I or Stage II, preferably the latter, were placed on a $BM_3$ solid medium. This medium has the same growth hormone concentration as $BM_2$, however, the osmoticant was raised to a much higher concentration. In this case the osmoticant, myo-inositol, was at a concentration of 10,000 mg/L or 1% on a w/v basis. Osmotic potential was measured as 240 mM/kg. Temperature and photoperiod were the same as for Stages I and II. After 3 or 4 subcultures of about 12–15 days each, very robust late stage proembryos had formed. These are characterized by smooth embryonal heads generally having in the neighborhood of over 100 individual cells with multiple suspensors, as exemplified in FIG. 2.

Osmotic potential of the late proembryo development medium should usually fall within the range of about 200–400 mM/kg. Most typically it should be in the neighborhood of about 1.5 times higher than that of the induction or multiplication media.

Alternatively, the Stage II proembryos could be cultured for late proembyro development in suspension in a liquid medium of similar composition to $BM_3$ but lacking the agar. In this case subcultures could be made every 7–8 days.

It is preferred that early stage proembryos brought into Stage III culture should have a Stage II subculturing for rapid multiplication of the particular clone. However, on occasions where time may be of greater importance than quantity, early stage proembryos from Stage I may be taken directly into Stage III.

Stage IV—Embryo Development

Figure 3:
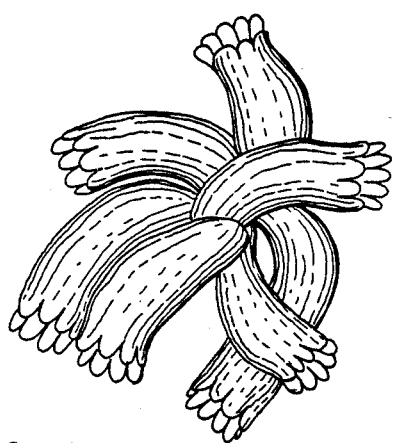
FIG. 3 depicts cotyledonary stage embryos.

The late stage proembryos from Stage III culture were transferred to a solid $BM_4$ medium. This medium either lacks growth hormones entirely or has them present only at very low levels and has the same lower level of osmoticants as Stages I and II. However, abscisic acid (5-(1-hydroxy-2,6,6-trimethyl-4-oxo-2-cyclohexene-1-yl)-3-methyl-2,4-pentadienoic acid) had been included here as a necessary material for further development. The osmotic potential of this medium will generally be no greater than about 175 mM/kg. In the present case it was measured as 168 mM/kg. As before, development was carried out in complete darkness at a temperature of 22°–25° C. Development time was 4–6 weeks after which elongated cotyledonary embryos 4–5 mm long were present. These appeared as represented in FIG. 3.

Stage V—Germination

Figure 4:
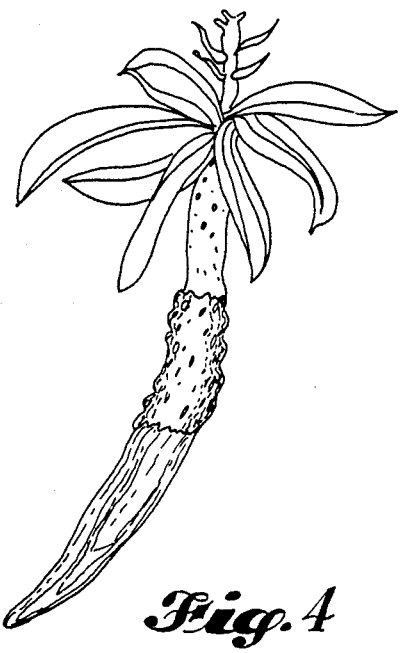
FIG. 4 shows a plantlet ready for transfer to soil.

Cotyledonary embryos fromm Stage IV were placed on solid $BM_5$ medium for germination. This is a basal medium lacking growth hormones which has been modified by reducing sucrose, myo-inositol and organic nitrogen. After about 6–8 weeks under environmental conditions of 23°–25° C. and a 16 hour light/8 hour dark photoperiod the resulting plantlets were approximately 20 mm in length and had a well developed radicle and hypocotyl and green cotyledonary structure and epicotyl as shown in FIG. 4.

Because of the reduced carbohydrate concentration, the osmotic potential of the germination medium is further reduced below that of the development medium. It will normally be below about 150 mM/kg and was, in the present example, about 100 mM/kg.

Stage VI—Plant growth

Plantlets from Stage V were removed from the culture medium and planted in a soil comprising equal parts of peat and fine perlite.

To the present time, three distinct genotypes of *Pinus taeda* have been successfully cultured through Stage V. Some of the plantlets have already been successfully transferred to soil and these are growing with good vigor. Two additional genotypes are being multiplied in Stage II prior to Stage III treatment. In work that preceeded that just described, all five genotypes when cultured without the Stage III high osmoticant treatment ultimately browned and died in Stage IV. Stated differently, the method failed completely when early stage *Pinus taeda* proembryos from Stage II were taken directly into Stage IV, as is taught in the prior art.

EXAMPLE 2

The critical secret of success of the present method lies in the early stage culturing of the early proembryos in a high osmoticant development medium. This is quite contrary to the accepted wisdom in the field of coniferous tissue culture where a raised osmoticant level was previously believed to be advantageous in the later stages of embryo development but was to be avoided in the early stages of culture.

In the work to date myo-inositol has proved to be somewhat superior to other osmoticants for the development of healthy Stage III late proembryos. However, other polyhydroxylated materials have also given very satisfactory results.

Cultures were made as above except that in Stage III 10,000 mg/L of either mannitol or sorbitol, or 30,000 mg/L of additional sucrose, was added to the $BM_2$ maintenance medium instead of the additional 9000 mg/L of myo-inositol described earlier. Osmolalities were measured as follows for the various Stage III media: myo-inositol—240 mM/kg; mannitol—242 mM/kg; sorbitol—238 mM/kg; and sucrose—265 mM/kg. When Stage II early stage proembryos were cultured on any of the above high osmoticant media, robust late stage proembryos developed that later were successfully cultured to the cotyledonary embryo stage.

It appears that most, if not all, sugars, hexitols, or cyclitols which can raise the osmotic potential to at least above 200 mM/kg will be satisfactory Stage III osmoticants. Other water soluble polyhydroxylated materials may also be suitable.

EXAMPLE 3

Some coniferous species are relatively easier to propagate by somatic embryogenesis than others. Coastel redwood, *Sequoia sempervirens*, is considered be be a relatively easy species while Norway spruce, *Picea abies*, is usually thought to be of only moderate difficulty. Most members of the genus Pinus as well as Douglas-fir, *Pseudotsuga menziesii*, are regarded as very difficult. This has posed a major challenge to researchers since the latter two genera include a major percentage of the worlds most economically important timber species. Even though past researchers have reported success with somatic embryogenesis of several pines and of Douglas-fir, others in the field have frequently not been able to duplicate the work of these competent investigators. There are probably several reasons for this. Most certainly, one of them is over optimism on the part of researchers who have achieved and reported early stage embryogenesis or embryo-like structures but who later have not been able to succeed in producing significant numbers of cotyledonary embryos or plantlets. Another is the great differences in performance between different genotypes within a given species. *Picea abies* is a case in point. As noted earlier it is usually regarded as a species of only moderate difficulty to reproduce by somatic embryogenesis using present state-of-the-art technology. However, there are some genotypes of *Picea abies* that haven proven intractable to all previous efforts. Most researchers have limited themselves to working with only one or two genotypes that are known from past experience to give good results.

The present method, which employs a new high osmoticant Stage III-type treatment of early stage proembryos, has resulted in successful production of late stage proembryos and cotyledonary embryos on 23 of the 26 genotypes of *Picea abies* that have been investigated to date. This sample includes a considerable number of previously intractable genotypes. As has been noted earlier, similar results have been obtained with *Pinus taeda*, although not all genotypes have been processed to the later stages of treatment to the present time. Excellent results have also been obtained with *Pseudotsuga menziesii* where 16 of 22 genotypes have developed cotyledonary embryos. Culturing on many of these genotypes is still in progress and has not advanced to the germination stage. However, to date plantlets from 5 genotypes have been transferred to soil resulting in at least 30 established plants.

While the plant growth hormone usages noted in Table 2 are near optimum for loblolly pine, different concentrations and mixtures may prove more suitable for other species. It is fairly well established that growth hormones are usually necessary in Stages I-III, although some workers have apparently achieved early stage proembyros using growth hormone-free media. However, even when initially cultured on hormone-free media, these early stage proembryos were then transferred to cultures having the usual growth hormones. These hormones may in some instances be a single auxin or a mixture of auxins with or without one or more cytokinins. As a general rule the total concentration of all growth hormones should be below about 250 $\mu$M/L, preferably below about 100 $\mu$M/L in the Stage I medium. These concentrations should be reduced about tenfold in the Stage II and Stage III media.

It should be recognized that there is not one single set of culturing conditions that will be suitable for achieving somatic embryogenesis of all species or for all genotypes within a species. Tissue culture as a whole is a highly unpredictable science. This statement has even greater applicability to somatic embryogenesis. Adjustments in the mineral and plant hormone constituents of the culture media must frequently be made depending on the particular species and genotype being cultured. This applies to each of the various stages of culturing from explants to plantlets. These adjustments are considered to be within the routine experimental capability of those skilled in the art of tissue culture. The new and critical discovery of the present invention is the use of a high osmoticant medium when culturing is still at the early proembryo stage. This has given results that are far superior in terms of success and consistency than any process reported heretofore. The process has been successfully applied to all of the several species and many genotypes of coniferous plants studied to date and appears to be of general use for all coniferous species.

It will be understood that many variations can be made in the procedures described for the various culturing stages while still retaining the necessary and critical high osmoticant early treatment stage. It is the intention of the inventors that such variations should be included within the scope of their invention if found defined within the following claims.

BIBLIOGRAPHY

Abo El-Nil, Mostafa, 1980 Embryogenesis of gymnosperm forest trees. U.S. Pat. No. 4,217,730.

Becwar, M. R., S. R. Wann, and R. Nagami, 1988 A survey of initiation frequency of embryogenic callus among ten families of *Pinus taeda* (loblolly pine). *Abstracts*, 4th International Conifer Tissue Culture Work Group, Aug. 8–12, 1988, Saskatoon, Saskatchewan, Canada.

Bourgkard, F. and J. M. Favre, 1988 Somatic embryos from callus of *Sequoia sempervirens*. *Plant Cell Reports* 7: 445–448.

Durzan, D. J. and P. K. Gupta, 1987 Somatic embryogenesis and polyembryogenesis in Douglas-fir cell suspension cultures. *Plant Science* 52: 229–235.

Cupta, Promod K. and Don J. Durzan,
  1985 Shoot multiplication from mature trees of Douglas-fir (*Pseudotsuga menziesii*) and sugar pine (*Pinus lambertiana*). *Plant Cell Reports* 4: 177–179.
  1986 Somatic polyembryogenesis from callus of mature sugar pine embryos. *Bio/Technology* 4: 643–645.
  1987 Biotechnology of somatic polyembryogenesis and plantlet regeneration in loblolly pine. *Bio/Technology* 5: 147–151.

Hakman, Inger and Sara von Arnold, 1985 Plantlet regeneration through somatic embryogenesis in *Picea abies* (Norway spruce). *Journal of Plant Physiology* 121: 149–158.

Hakman, Inger, Larry C. Fowke, Sara von Arnold, and Tage Eriksson, 1985 The development of somatic embryos in tissue cultures initiated from immature embryos of *Picea abies* (Norway spruce). *Plant Science* 38: 33–35.

Murashige, T. and F. Skoog, 1962 A revised medium for rapid growth and bioassays with tobacco tissue cultures. *Physiologia Plantarum* 15: 473–493.

Nagmani, R. and J. M. Bonga. 1985 Embryogenesis in subcultured callus of *Larix decidua*. *Canadian Journal of Forest Research* 15: 1088–1091.

Nagmani, R and M. R. Becwar, 1988 Factors affecting somatic embryo development in loblolly pine. *Abstracts*, 4th International Conifer Tissue Culture Work Group, Aug. 8–12, 1988, Saskatoon Saskatchewan, Canada.

Singh, Hardev, 1978 "Embryo" in *Embryology of Gymnosperms*, Chapter 11, Gebruder Borntrager, Berlin.

Teasdale, Robert D., Pamela A. Dawson, and Harold W. Woolhouse. 1986 Mineral nutrient requirements of a loblolly pine. (*Pinus taeda* cell suspension culture. *Plant Physiology* 82: 942–945.

We claim:

1. A method for reproducing coniferous plants by somatic embryogenesis which comprises;
    placing a suitable explant on an induction culture medium with a sufficient amount of plant growth hormones and relatively low in osmoticants and growing a culture containing early stage proembryos, the osmotic potential of said induction medium being below about 175 mM/kg; and
    transferring the early sttage proembryos from the induction culture to a late stage proembryo development culture medium having a sufficient amount of plant growth hormones and a significantly increased concentration of osmoticants for a sufficient time and under suitable environmental conditions for development of late stage proembryos, said development culture having an osmotic potential in the range of about 200–400 mM/kg.

2. The method of claim 1 which further includes removing the late stage proembryos and placing them on a development medium having a reduced level of osmoticant but containing a sufficient amount of abscisic acid with plant growth hormones being reduced to very low levels or entirely absent, the osmotic potential being below about 175 mM/kg,
    maintaining said proembryos for a sufficient time and under suitable environmental conditions to enable development of cotyledonary embryos, and
    removing the cotyledonary embryos to a germination medium essentially lacking plant growth hormones and low in organic nitrogen and osmoticants to enable further growth of the cotyledonary embryos into plantlets, the osmotic potential of the germination medium being below about 150 mM/kg.

3. The method of claim 1 which further includes subculturing the early stage proembryos from the induction culture medium on a maintenance and multiplication medium having a sufficient amount of plant growth hormones prior to further culturing said early stage proembryos on the late stage proembryo development culture medium.

4. The method of claim 2 which further includes subculturing the early stage proembryos from the induction culture medium on a maintenance and multiplication medium having a sufficient amount of plant growth hormones prior to further culturing said early stage proembryos on the late stage proembryo development culture medium.

5. The method of claim 1 in which the osmoticant is a selected from the group consisting of sugars and hexitols.

6. The method of claim 5 in which the sugar is sucrose.

7. The method of claim 5 in which the hexitol is selected from the group consisting of sorbitol and mannitol.

8. The method of claim 5 in which the hexitol is a cyclitol.

9. The method of claim 8 in which the cyclitol is myo-inositol.

10. The method of claim 1 in which the coniferous plant is selected from the family Pinaceae.

11. The method of claim 10 in which the plant is selected from the genus Pinus.

12. The method of claim 11 in which the plant is *Pinus taeda*.

13. The method of claim 10 in which the plant is *Pseudotsuga menziesii*.

14. The method of claim 10 in which the plant is *Picea abies*.

15. The method of claim 1 in which the explant is a zygotic embryo excised from a seed.

16. The method of claim 15 in which the seed is immature.

17. The method of claim 15 in which the seed is mature.

18. The method of claim 1 in which the plant growth hormones in the induction medium comprise at least one auxin in a concentration not exceeding about 250 µM/L.

19. The method of claim 1 in which the plant growth hormones comprise a mixture of at least one auxin and one cytokinin in a total concentration which does not exceed about 250 μM/L.

20. The method of claim 19 in which the total concentration of auxins and cytokinins does not exceed about 100 μM/L.

21. The method of claim 18 in which the concentration of plant growth hormones in the late stage proembryo development culture medium is reduced by a factor of about 10 below the concentration in the induction medium.

22. The method of claim 19 in which the concentration of plant growth hormones in the late stage proembryo development culture medium is reduced by a factor of about 10 below the concentration in the induction medium.

23. The method of claim 3 in which the concentration of plant growth hormones in the maintenance and multiplication culture medium is reduced by a factor of about 10 below the concentration in the induction medium.

24. The method of claim 4 in which the concentration of plant growth hormones in the maintenance and multiplication culture medium is reduced by a factor of about 10 below the concentration in the induction medium.

* * * * *